United States Patent
Sugita

(10) Patent No.: US 7,248,729 B2
(45) Date of Patent: Jul. 24, 2007

(54) IMAGE PROCESSING APPARATUS AND IMAGE PROCESSING METHOD

(75) Inventor: Moyo Sugita, Kaisei-machi (JP)

(73) Assignee: Fujifilm Corporation, Tokyo (JP)

( * ) Notice: Subject to any disclaimer, the term of this patent is extended or adjusted under 35 U.S.C. 154(b) by 681 days.

(21) Appl. No.: 10/797,039

(22) Filed: Mar. 11, 2004

(65) Prior Publication Data

US 2004/0182991 A1 Sep. 23, 2004

(30) Foreign Application Priority Data

Mar. 20, 2003 (JP) ............................. 2003-076945

(51) Int. Cl.
*G06K 9/00* (2006.01)
(52) U.S. Cl. .................................. 382/132; 250/208.1
(58) Field of Classification Search ................ 382/128, 382/129, 130, 131, 132, 133, 134; 378/46, 378/90, 92, 98.4, 98.6, 101; 250/370.09, 250/208.1; 600/300
See application file for complete search history.

(56) References Cited

U.S. PATENT DOCUMENTS 5,339,815 A * 8/1994 Liu et al. .................... 600/437
6,198,844 B1 * 3/2001 Nomura ....................... 382/168
6,349,227 B1 * 2/2002 Numada ...................... 600/310

FOREIGN PATENT DOCUMENTS

| JP | 07-271972 A | 10/1995 |
| JP | 09-097321 A | 4/1997 |
| JP | 10-071138 A | 3/1998 |

* cited by examiner

*Primary Examiner*—Samir Ahmed
*Assistant Examiner*—Abolfazl Tabatabai
(74) *Attorney, Agent, or Firm*—Sughrue Mion, PLLC

(57) ABSTRACT

An image processing apparatus and method capable of automatically performing the blackening processing of a blank area and/or a scattering area even in a mammograph obtained by radiation imaging. The image processing apparatus includes: a profile data calculating unit for receiving image data obtained by imaging an object to calculate pieces of profile data corresponding to change of brightness among a plurality of pixels; a binarizing unit for binarizing each of the piece of profile data obtained by the profile data calculating unit; a convex closure processing portion for performing convex closure processing on the pieces of profile data binarized by the binarizing unit to extract an outermost profile; and blackening processing means for performing blackening processing the received image data to reduce brightness of pixels in an area out of the outermost profile extracted by the convex closure processing portion.

6 Claims, 9 Drawing Sheets

100  101

IMAGE PROCESSING APPARATUS AND IMAGE PROCESSING METHOD

BACKGROUND OF THE INVENTION

1. Field of the Invention

The present invention relates to an image processing apparatus and an image processing method for processing image data, which is obtained by imaging such as radiation imaging, to display or output images.

2. Description of a Related Art

Conventionally, an imaging method using a radiation (X-ray, α-ray, β-ray, γ-ray, electron beam, ultraviolet ray and so on) has been utilized in various fields, and particularly, employed as one of the most important means for diagnosis in a medical field. Since a first X-ray photograph was realized, X-ray photography has been repeatedly improved. At present, a method using a combination of a fluorescent screen and an X-ray film has become a main stream. On the other hand, in recent years, various digitized apparatuses such as X-ray CT apparatus, ultrasonic imaging apparatus, and MRI apparatus are in practical use. And diagnosis information processing system is now under progression in hospitals. Also, as for X-ray images, many studies have been made for digitizing the systems, and a radiation imaging method using photostimulable phosphor has been established, which attracts attentions as a method that will replace the conventional X-ray photography.

The photostimulable phosphor (storage phosphor) is a substance which accumulates a part of radiation energy when irradiated with a radiation, and after that, emits stimulated fluorescence corresponding to the accumulated energy when irradiated with an excitation light such as visible light. The existence of the photostimulable phosphor is previously known. The radiation imaging method using the photostimulable phosphor will be described below. That is, by using a radiation imaging apparatus and a sheet which is applied with photostimulable phosphor, radiation imaging is carried out on an object to be imaged such as human body to record radiation image information on the photostimulable phosphor sheet. Then, using an image reading apparatus, the radiation image information is read out from the photostimulable phosphor sheet. That is, in the image reading apparatus, when the photostimulable phosphor sheet is scanned with an excitation light such as laser beam, photostimulable luminescent light is generated from the photostimulable phosphor. By detecting the light in a photoelectrical manner, the image data is generated. Further, after being appropriately processed with an image processing apparatus, the image data is output to a display such as a CRT, or printed out on a film with a laser printer or the like. Thus, the radiation image can be displayed as a visible image.

In view of imaging sensitivity and image quality, the radiation imaging method as described above has the performance comparable to the conventional X-ray photography. For example, compared to the conventional X-ray photography, the exposure latitude is extremely wider and the response of the photostimulable luminescent light with respect to the exposure intensity is substantially proportional all over the entire exposure range. Therefore, even when the object is imaged with any radiation dose, light-emitting area, where an image resides, can be covered and satisfactorily normalized to obtain digitalized signals. Further, by processing signals obtained as described above with an appropriate image processing method, images with satisfactory quality can be stably provided even under a variety of imaging conditions. Furthermore, since digitalized image information is directly obtained, large-scale data can be stored for a long time period without deterioration of the images and development to a medical diagnosis information system becomes possible.

The radiation imaging method as described above is applied to the radiation imaging of mammae (mammography), which is carried out in breast cancer diagnosis or the like. Visible images obtained by the radiation imaging are displayed on a monitor screen or printed out on a film to be used for medical diagnosis.

However, in the images obtained by the radiation imaging, a blank area having a high brightness occasionally occurs. FIG. 10 shows a mammograph. As shown in FIG. 10, a blank area 101 is generated along with a radiation image of a mamma area 100.

The reason why such blank area is generated in the mammograph is as described below. In the image reading apparatus, which reads out radiation image while conveying a sheet applied with photostimulable phosphor, a misalignment occasionally occurs on the sheet under transportation. In order to avoid such problem that the entire image data of a desired image area (for example, mamma area 100) cannot be obtained due to the misalignment during the conveyance, the start timing of the reading is adjusted to delay so that the entire image data of a desired image area is obtained. At that time, the adjustment to delay the start timing of the reading leads to such situation that an area out of the sheet is read out. That area is visualized on the film resulted in a transparent blank area 101. Since light is projected from the backside of the film when observing the radiation image, such blank area 101 appears as an area of a high brightness. Accordingly, there arises such problems that the visibility is reduced and eyestrain is caused.

As a related art, Japanese Unexamined Patent Application Publication JP-A-7-271972 discloses an image processing apparatus, in which at least an interested area in an output image is outputted at a desired density and/or tone in accordance with the purpose of diagnosis with an simple operation (pp. 4-6, FIG. 1). In this image processing apparatus, the density and/or tone in the radiation image can be set, and based on the set density and/or tone, a desired radiation image can be outputted. However, in the image processing apparatus disclosed in JP-A-7-271972, the desired interested area in radiation image to be displayed has to be set up by using a mouse, a keyboard or the like.

Further, Japanese Unexamined Patent Application Publication JP-A-9-97321 discloses the following image displaying method. That is, in an image displaying apparatus for displaying images, which are taken by use of an irradiation field stop, on a light-emitting display means such as CRT so that the brightness level of the area outside the irradiation field is higher than the brightness level of the area inside the irradiation field, reduction of contrast in the area inside the irradiation field, which is caused from scattered light from the area outside the irradiation field, is prevented (pp. 4-5, FIG. 1). In this image displaying method, as for the area where the image signal level is higher than a predetermined threshold value, the higher the image signal level becomes the lower the brightness level is set to, while as for the area where the image signal level is lower than the predetermined threshold value, the brightness level is set to a minimum brightness level. Thereby, the area outside the irradiation field, where the image signal level is low (the brightness level is high), is blackened to prevent contrast in the area inside the radiation field from being reduced.

However, in the mammograph, there is a possibility that a scattering area, where the brightness level becomes the same level as that of the area inside the irradiation field by reading out excitation light scattered by an edge of the photostimulable phosphor sheet, may reside in between the area inside the irradiation field and the area outside the irradiation field. Accordingly, even when the image displaying method disclosed in JP-A-9-97321 is applied to the mammography, the scattering area as described above cannot be blackened. Also, in this image displaying method, the area outside the irradiation field is detected only by comparing the image signal level with the threshold value. Accordingly, there is a possibility that the area inside the irradiation field where the image signal level is low (brightness level is high) might be blackened.

Furthermore, Japanese Unexamined Patent Application Publication JP-A-10-71138 discloses a radiation image processing apparatus, in which re-imaging is not required even when an error occurs in automatic recognition of area inside the irradiation field, and load of processing for recognizing the irradiation field is made smaller, while keeping anti-dazzle effect during observation of image (pp. 4-6, FIG. 3). In this radiation image processing apparatus, points, where the image data changes sharply to substantially zero, are determined as the boundary points between the area inside the irradiation field and the area outside the irradiation field. By connecting these boundary points, the boundary line is determined. And an external area of the boundary line is recognized as the area outside the irradiation field so as to perform the blackening processing.

However, in the mammograph, no points are included in some directions where the image data changes sharply to substantially zero from the center to the periphery thereof, as the mamma area 100 and the blank area 101 shown in FIG. 10. Accordingly, even when the radiation image processing apparatus disclosed in JP-A-10-71138 is applied to the mammography, there may be a case where the boundary line cannot be determined. According to this radiation image processing apparatus, however, in the case where a range of the area outside the irradiation field that has been automatically recognized is not true, the blackening processing can be made in an appropriate range by manually correcting the automatically recognized range while monitoring the image.

SUMMARY OF THE INVENTION

The present invention has been achieved in view of the above-described problems. An object of the present invention is to provide an image processing apparatus and an image processing method capable of automatically performing the blackening processing of the blank area and/or the scattering area in a mammograph obtained by the radiation imaging.

In order to solve the above-described problems, an image processing apparatus according to the present invention comprises: profile data calculating means for receiving image data obtained by imaging an object to calculate pieces of profile data corresponding to change of brightness among a plurality of pixels; binarizing means for binarizing each of the pieces of profile data obtained by the profile data calculating means; convex closure processing means for performing convex closure processing on the pieces of profile data binarized by the binarizing means to extract an outermost profile; and blackening processing means for performing blackening processing on the received image data to reduce brightness of pixels in an area out of the outermost profile extracted by the convex closure processing means.

Also, an image processing method according to the present invention comprises the steps of: (a) receiving image data obtained by imaging an object to calculate pieces of profile data corresponding to change of brightness among a plurality of pixels; (b) binarizing each of the pieces of profile data obtained at step (a); (c) performing convex closure processing on the pieces of profile data binarized at step (b) to extract an outermost profile; and (d) performing blackening processing on the received image data to reduce brightness of pixels in an area out of the outermost profile extracted at step (c).

According to the present invention, the profile data corresponding to change of brightness among a plurality of pixels is binarized, and then subjected to the convex closure processing to extract the outermost profile. Accordingly, on a mammograph obtained by radiation imaging, by extracting an outermost profile of a mamma area, the blackening processing of the blank area and/or the scattering area can be performed automatically.

DESCRIPTION OF THE PREFERRED EMBODIMENTS

Figure 1:
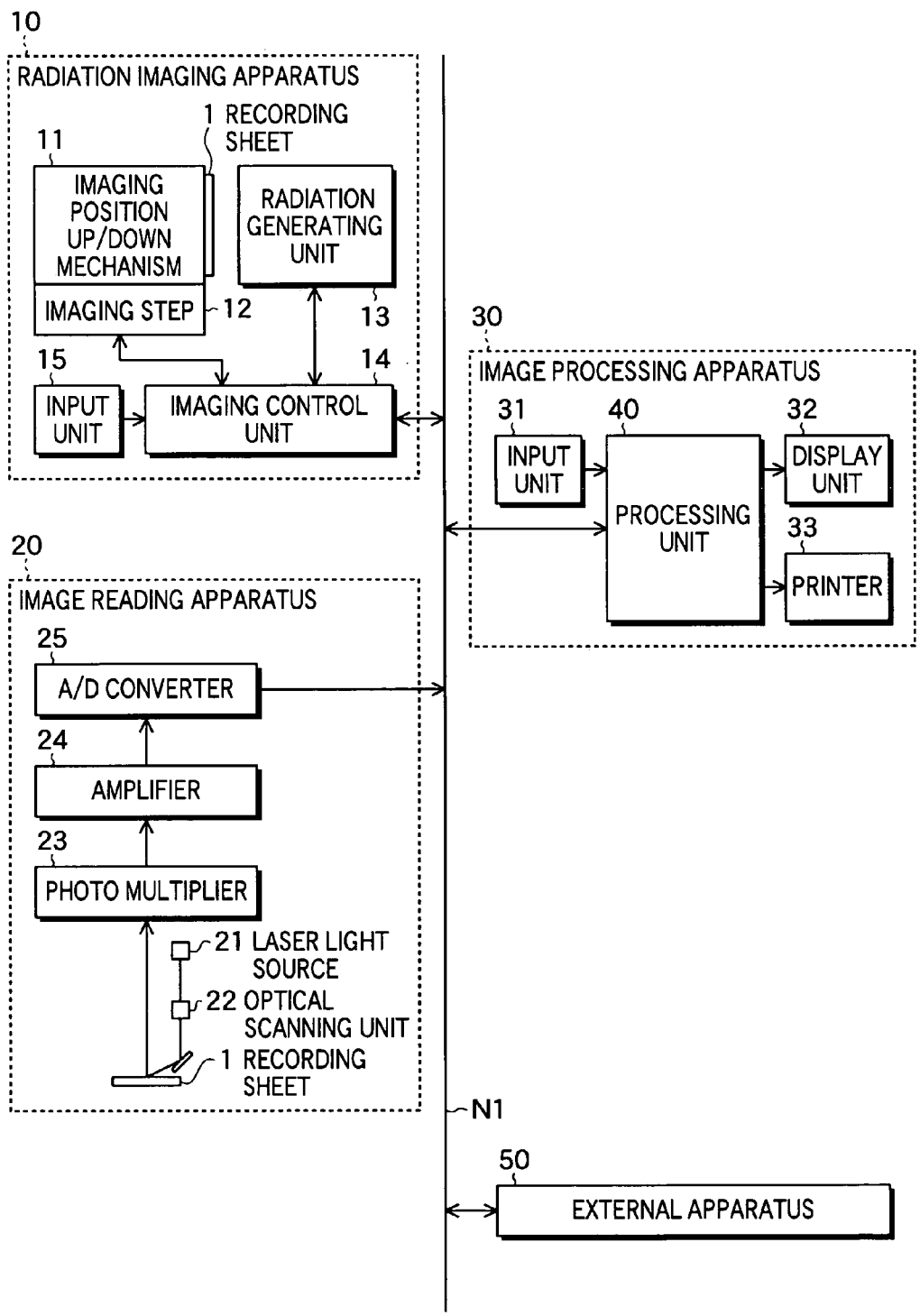
FIG. 1 is a block diagram showing the configuration of a radiation imaging system including an image processing apparatus according to one embodiment of the present invention.

Embodiments of the present invention will be described in detail below by referring to the drawings. The same constituent elements will be given with the same reference numerals and the descriptions thereof will be omitted.

FIG. 1 is a block diagram showing the configuration of a radiation imaging system including an image processing apparatus according to one embodiment of the present invention. As shown in FIG. 1, the radiation imaging system comprises a radiation imaging apparatus 10 for irradiating an object with a radiation to perform imaging thereby recording a radiation image on a recording sheet (photostimulable phosphor sheet) 1, an image reading apparatus 20 for reading out information such as radiation image recorded on the recording sheet 1 in a photoelectric manner to generate image data, and an image processing apparatus 30 for receiving the image data from the image reading apparatus 20 to, perform various processing thereby displaying or outputting an image. Further, if required, external device 50 such as a data base server, an ID card reader, or a terminal device is connected to a network N1.

The radiation imaging apparatus 10 includes an imaging position up/down mechanism 11 that moves up/down the position of the recording sheet 1 to raise or lower the position where the object is imaged, an imaging step 12 that positions the feet of the object, a radiation generating unit 13 that irradiates the object with a radiation, an imaging control unit 14 that controls the radiation generating unit 13 and so on in accordance with given imaging conditions, and an input unit 15 that is used for inputting various commands and imaging conditions. The imaging control unit 14 is connected to the network N1 so that the imaging conditions may be set up through the network N1.

The recording sheet 1, which is used for radiation imaging, includes a base material applied with a photostimulable phosphor substance. When the sheet is irradiated with a radiation, information of the object is recorded thereon. Radiation imaging of the object is carried out under predetermined imaging conditions and the radiation image is recorded on the recording sheet 1. After imaging, the recording sheet 1 is set in a predetermined position of the image reading apparatus 20.

In the image reading apparatus 20, the light beam emitted from a laser light source 21 scans the surface of the recording sheet 1 through an optical scanning unit 22. Owing to this scanning, the recording sheet 1 is irradiated with the light beam to allow photostimulable luminescent light having light intensity corresponding to accumulated and recorded radiation image information to generate from a portion where is irradiated with the light beam. The photostimulable luminescent light is detected by a photo multiplier 23 in a photoelectrical manner to be output as an analog signal, which is amplified by an amplifier 24 and digitalized by an A/D converter 25. The image data generated as described above is transmitted to the image processing apparatus 30 along with image incidental information, which is incident to the image, through the network N1.

The image processing apparatus 30 includes an input unit 31 that is used for inputting numeral values, commands and so on, a display unit 32 that displays images, a printer 33 that prints out images on a film or the like and a processing unit 40. The processing unit 40 processes the received image data.

Figure 2:
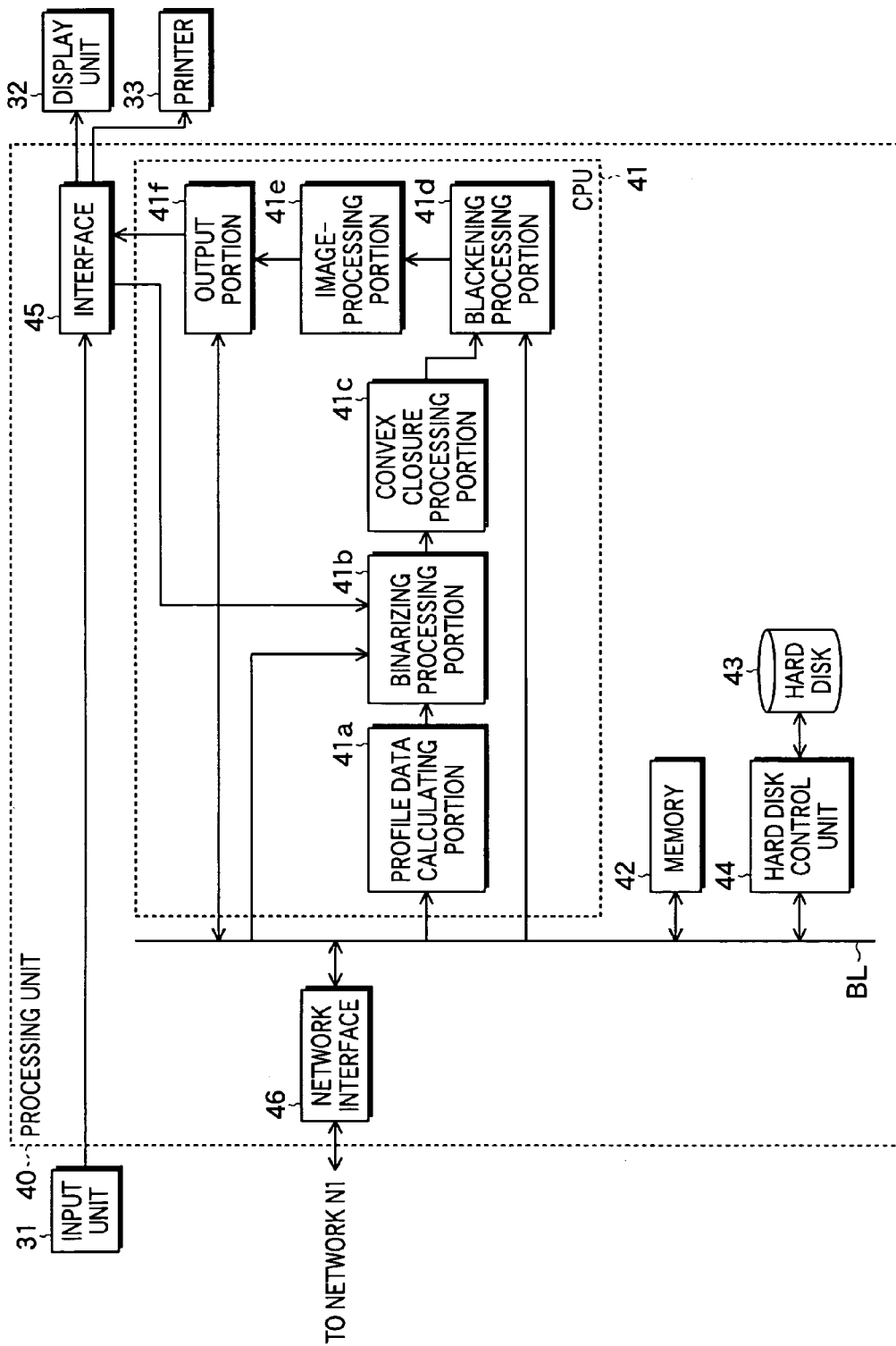
FIG. 2 is a block diagram showing a detailed configuration of the image processing apparatus shown in FIG. 1.

FIG. 2 is a block diagram showing a detailed configuration of the image processing apparatus 30 as shown in FIG. 1. The processing unit 40 includes a central processing unit (referred to as CPU) 41, a memory 42 that contemporarily stores the received image data and the image incidental information, a hard disk 43 as a recording medium, a hard disk control unit 44, an interface 45 and a network interface 46. These are connected to each other through a bus line BL.

The CPU 41 is connected to the input unit 31 such as a keyboard and a mouse, the display unit 32 such as a CRT display and the printer 33 though the interface 45. And also, the CPU 41 is connected to the radiation imaging apparatus 10 and the image reading apparatus 20 though the network interface 46 and the network N1. In the hard disk 43, software (program) for operating the CPU 41 is stored. As for the recording medium, in addition to the internal hard disk 43, an external hard disk, a flexible disk, MO, MT, RAM, CD-ROM, DVD-ROM or the like may be used.

Figure 3:
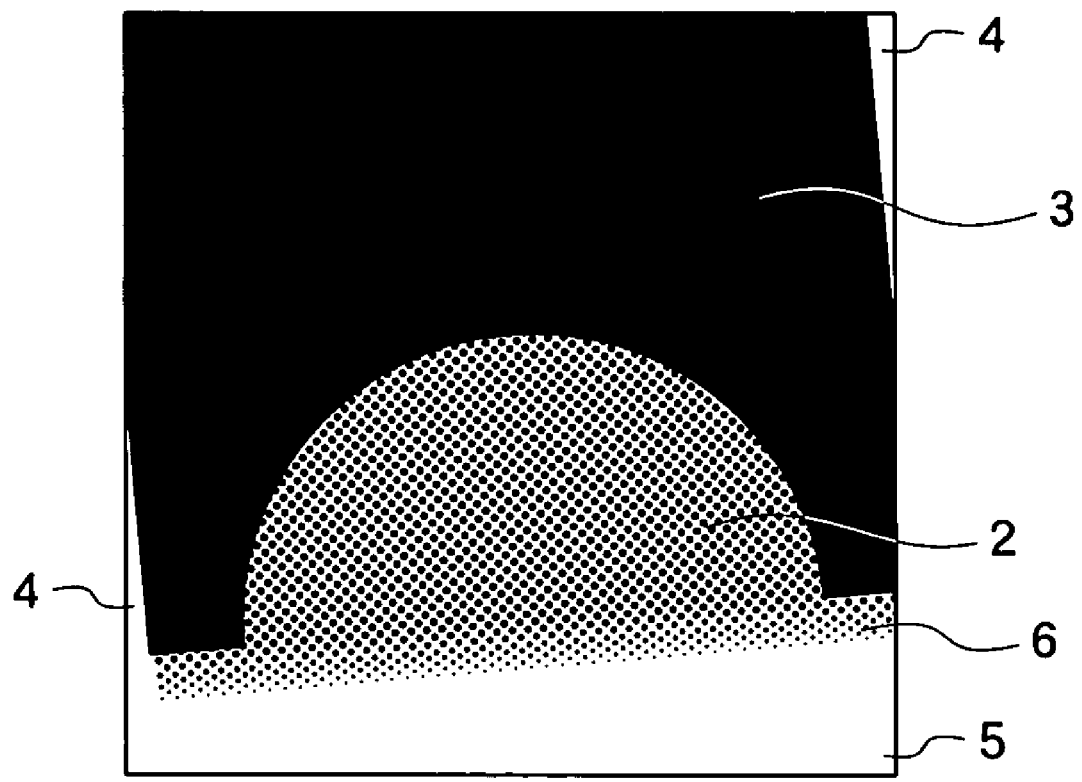
FIG. 3 is a diagram showing an example of an image which is represented by image data transmitted from an image reading apparatus to the image processing apparatus.

Next, the function blocks 41a-41f, which are constituted of the CPU 41 and the software (program), will be described. FIG. 3 shows an example of an image represented by the image data transmitted from the image reading apparatus to the image processing apparatus. This image includes a mamma area 2, an area out of mamma 3, an area outside an irradiation field 4 which is generated by scanning a displaced sheet with the light beam, a blank area 5 which is generated by reading the sheet with delayed start timing, and a scattering area 6.

The profile data calculating portion 41a calculates pieces of profile data on the basis of the received image data by using a Sobel filter. The Sobel filter is a filter for obtaining profile data corresponding to change of brightness among a plurality of pixels by performing the following calculation. That is, values of total nine neighboring pixels, which include a target pixel and pixels adjacent to the target pixel, are respectively multiplied by predetermined coefficients and the sum thereof is obtained.

Figure 4A:
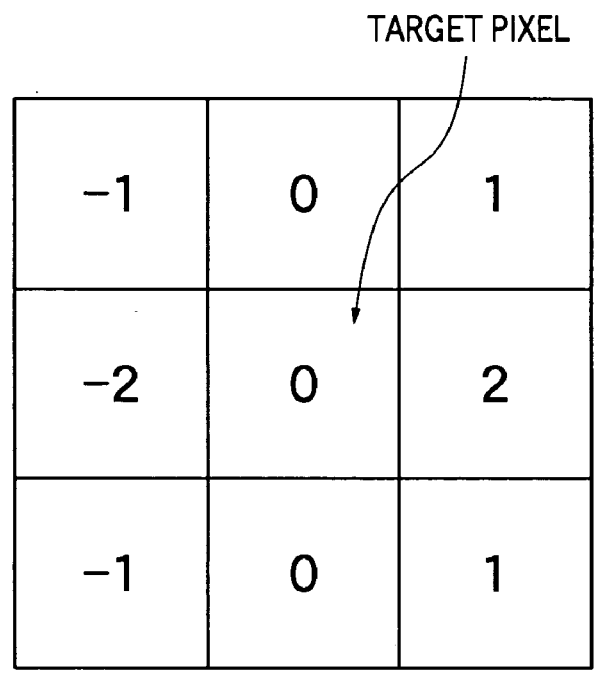
FIGS. 4A and 4B are diagrams showing examples of coefficients of a Sobel filter.
Figure 4B:
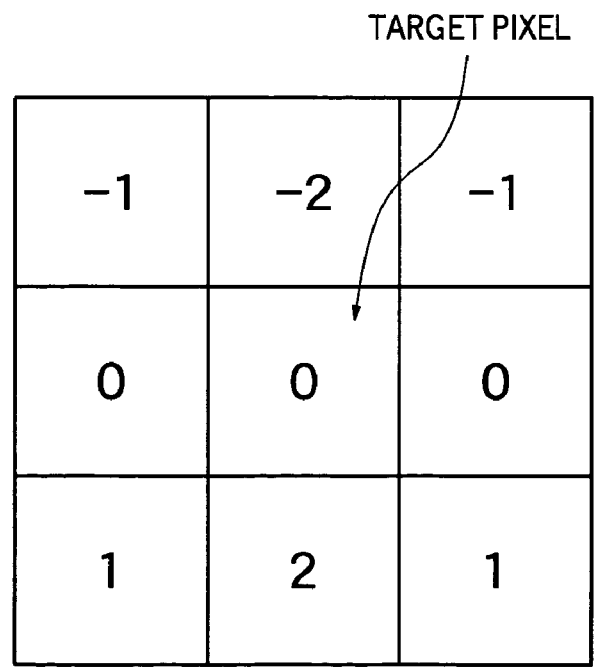

FIGS. 4A and 4B show examples of coefficients of the Sobel filter. FIG. 4A shows coefficients for extracting the profile in the vertical direction. FIG. 4B shows coefficients for extracting the profile in the horizontal direction. In the respective directions, a portion having a large change in pixel values results in a large absolute value of the sum. While a portion having a small change in pixel values results in a small absolute value of the sum. Accordingly, by connecting the pixels to each other, which have a large absolute value of the sum, the profile of the respective areas can be extracted.

According to the changes of pixel values or the characteristics of the profile to be extracted, the coefficients shown in either one of FIGS. 4A and 4B may be used, or the combination thereof may be used. Further, the profile may be extracted on the basis of the summed value with signs, instead of the summed absolute value.

For example, the profile can be extracted on the basis of a summed value with a sign, which value is obtained by using the coefficients as shown in FIG. 4A. Also, the profile can be extracted on the basis of an absolute summed value, which value is obtained by using the coefficients as shown in FIGS. 4A and 4B. In place of the Sobel filter, it may be arranged so as to use a Prewitt filter or the like.

Figure 5:
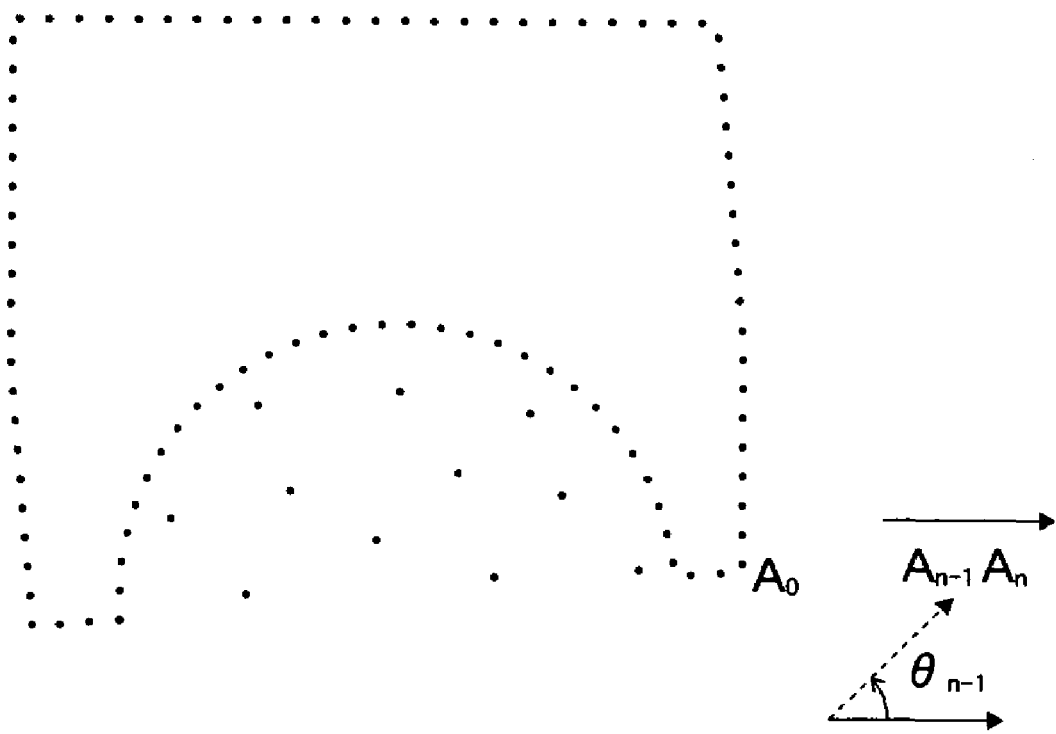
FIG. 5 is a diagram showing an image represented by binarized profile data.

Referring to FIG. 2 again, a binarizing processing portion 41b performs binarizing processing on pieces of profile data, which has been obtained by the profile data calculating portion 41a, on the basis of a threshold value inputted by using the input unit 31 or a threshold value recorded in the hard disk 43 or the like. Owing to this, pieces of binarized profile data, which represents an image as shown in FIG. 5, is obtained.

The convex closure processing portion 41c performs convex closure processing on the pieces of binarized profile data to extract an outermost profile. Here, the convex closure processing will be described. By carrying out the convex closure processing on an image as shown in FIG. 5 which includes a plurality of points, a plurality of line segments connecting the outermost profile points is obtained. As a result, a plurality of line segments, which connects one point to another point, enclose all other points. In the figure enclosed by these line segments, no concave portion is included.

Figure 6:
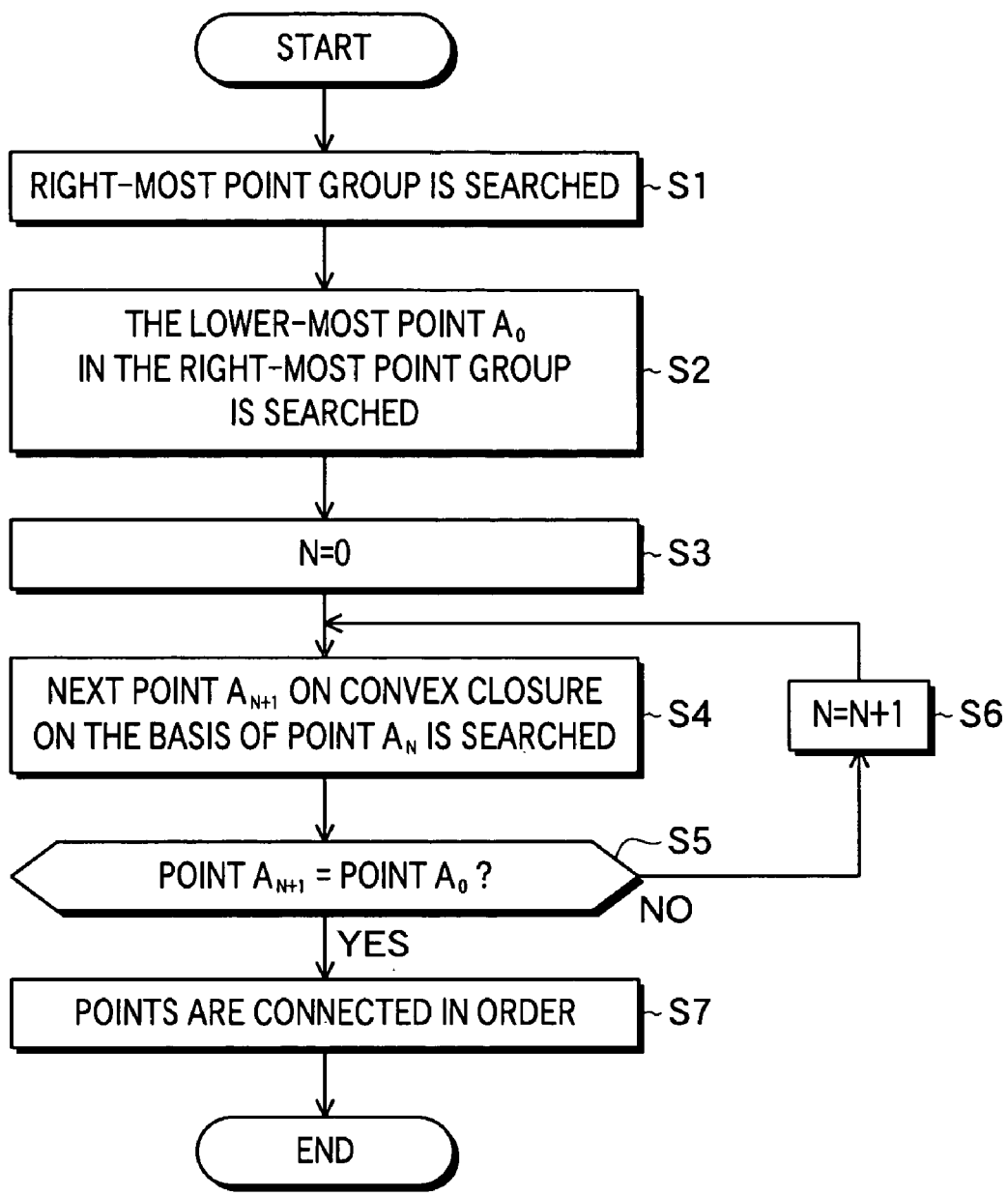
FIG. 6 is a flowchart for illustrating convex closure processing.

FIG. 6 is a flowchart for explaining the convex closure processing. First of all, at steps S1 and S2, a point is searched which is positioned at the right-lowest point in the plurality of points as shown in FIG. 5. That is, at step S1, a group of points at the right most (right-most point group) is searched. Further, at step S2, a point A0, which is positioned at the lowest in the right-most point group, is searched. Accordingly, the point $A_0$ is determined as the right-lowest point.

Then, at steps S3-S6, using the point $A_0$ as the initial point, every point on the convex closure is searched. That is, at step S3, the variable N is set to zero as the initial value. Further, at step S4, on the basis of a point $A_N$, the next point $A_{N+1}$ on the convex closure is searched. Here, an angle formed by a line connecting the point $A_N$ and the next point $A_{N+1}$ from the X-axis is defined as an angle $\theta_N$. In the case of N=0, a point making an angle $\theta_0$ have a smallest positive value is determined as a point $A_1$. In the case of N>1, a point making an angle $\theta_N$ have a smallest positive value larger than $\theta_{N-1}$ is determined as a point $A_{N+1}$.

At step S5, it is determined whether or not the searched point $A_{N+1}$ is the same point as the initial point $A_0$. When the searched point $A_{N+1}$ is not the same point as the initial point $A_0$, the processing proceeds to step S6 where the variable N is increased by 1 and the processing proceeds to step S4. When the searched point $A_{N+1}$ is the same point as the initial point $A_0$, the processing proceeds to step S7 where the searched points are connected to each other with a line in order to terminate the convex closure processing.

Figure 7:
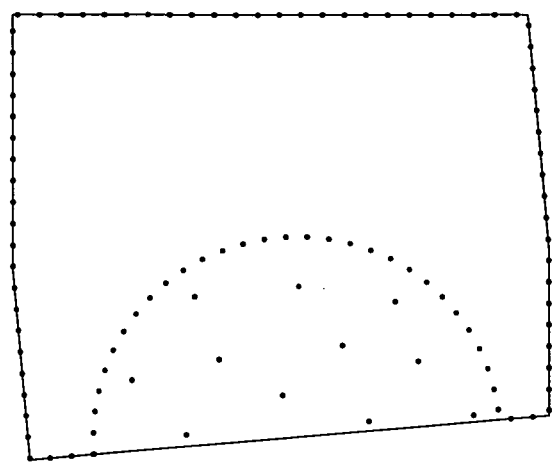
FIG. 7 is a diagram showing an image of which outermost profile is extracted by the convex closure processing.

Owing to this, as shown in FIG. 7, the outermost profile can be extracted. The line which is connected at step S7 (outermost profile line) may be a set of lines connecting two outermost profile points searched consecutively, or a set of curved lines connecting three or more outermost profile points searched consecutively, or a set of lines averaged on the basis of three or more outermost profile points searched consecutively.

Figure 8:
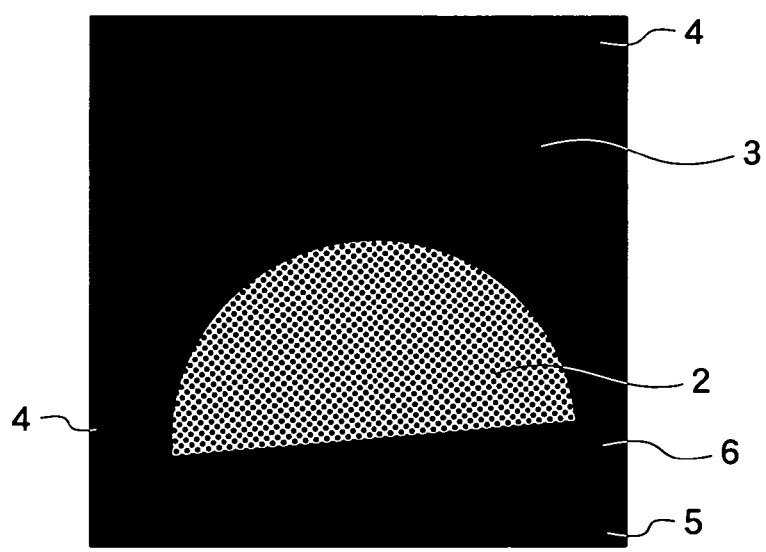
FIG. 8 is a view showing an image which has been subjected to blackening processing.

Referring to FIG. 2 again, the blackening processing portion 41d performs the blackening processing on the received image data on the basis of the profile data of the outermost profile, which is obtained by the convex closure processing, with respect to the area outside the irradiation field 4, the blank area 5, and the scattering area 6 as shown in FIG. 3. FIG. 8 is a view showing an image which has been subjected to the blackening processing. As described above, by appropriately selecting the threshold value for binarizing processing in the binarizing processing portion 41b, not only the area outside the irradiation field 4 and blank area 5 but also the scattering area 6, if any, can be subjected to the blackening processing.

The image processing portion 41e performs various image processing such as normalization and gradation processing on the image data which has been subjected to the blackening processing. The image data, which has been subjected to the image processing, is output from an output portion 41f to the display unit 32 or the printer 33 through the interface 45, and the image is displayed on the display or printed out on a film or the like. Also, the image data and the image incidental information are stored in the hard disk 43. It may be arranged so that the image processing such as the normalization and the gradation processing may be performed prior to the blackening processing.

The blackening processing in this embodiment may be performed on the entire image which is represented by the received image data. Alternatively, it may be arranged so that the blackening processing is performed on a partial area of the image which is represented by the received image data, while conventional blackening processing is performed on the other area. In the later case, the conventional blackening processing may be performed prior to or after the blackening processing according to this embodiment. Further, in the case of an imaging portion where the blank area causes no problem, the blackening processing of this embodiment may be omitted on the basis of the information of the portion included in the image incidental information, which is temporarily stored in the memory 42, or the like.

In this embodiment, each of the profile data calculating portion 41a, the binarizing processing portion 41b, the convex closure processing portion 41c, the blackening processing portion 41d, the image processing portion 41e, and the output portion 41f is constituted of a CPU and the software. However, they may be constituted of a digital circuit or an analog circuit.

Figure 9:
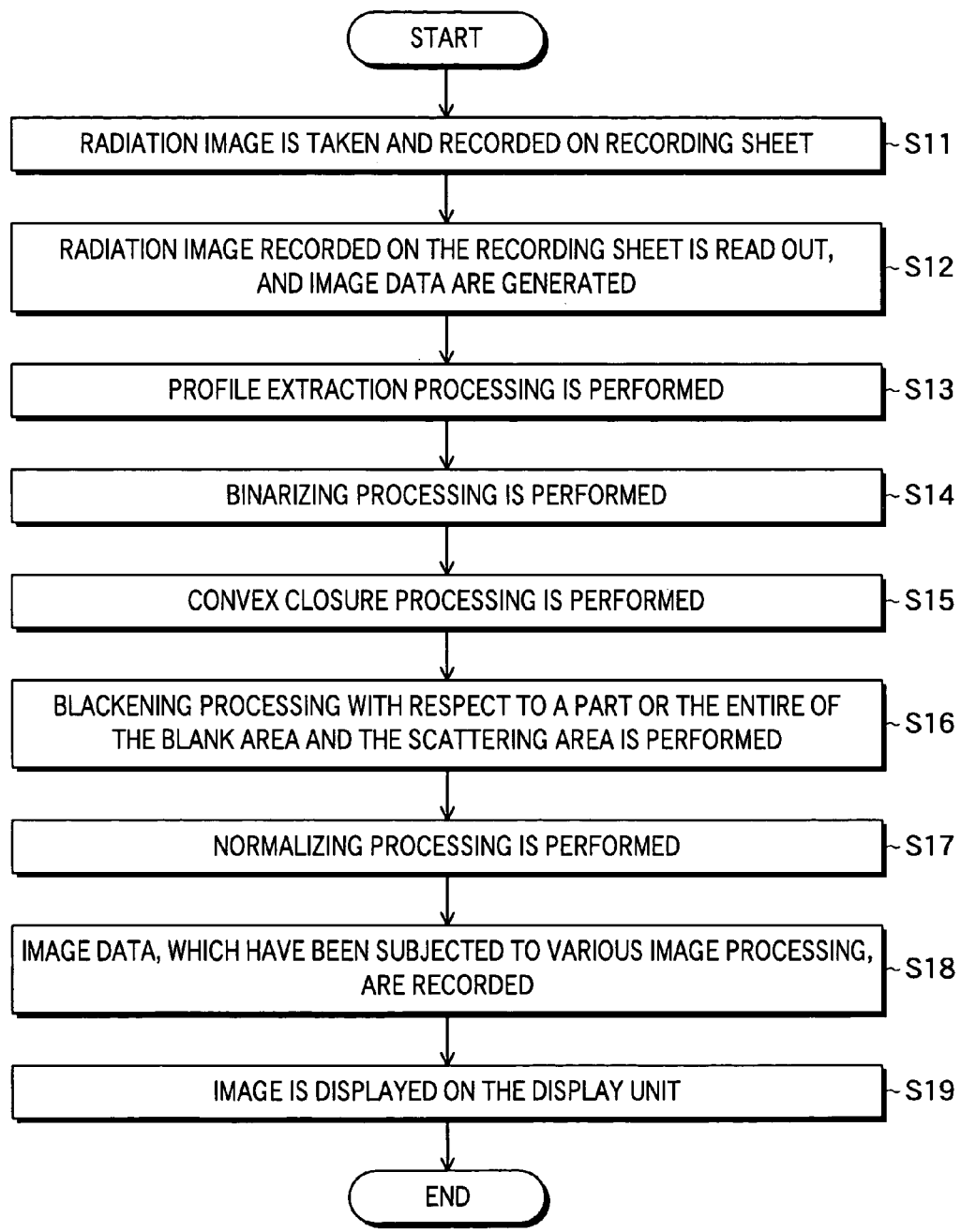
FIG. 9 is a flowchart showing the operation of the radiation imaging system including the image processing apparatus according to one embodiment of the present invention.
Figure 10:
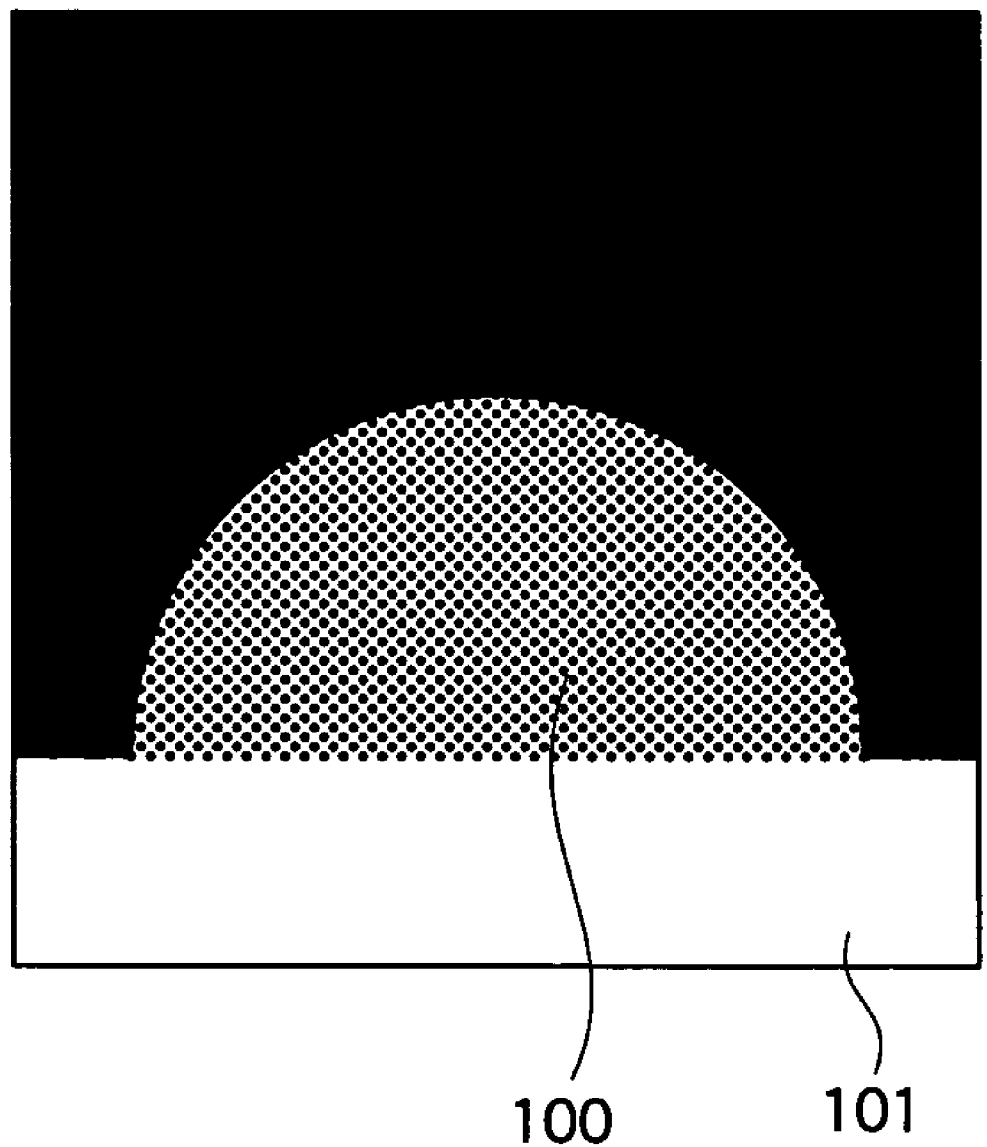
FIG. 10 is a diagram showing a mammograph.

Next, the operation of the radiation imaging system will be described with reference to FIGS. 1-2 and FIG. 9. FIG. 9 is a flowchart showing the operation of the radiation imaging system including the image processing apparatus according to this embodiment.

At step S11, the radiation imaging apparatus 10 irradiates an object with the radiation to obtain a radiation image and records the radiation image on the recording sheet 1. At step S12, the image reading apparatus 20 reads out the radiation image recorded on the recording sheet 1 and generates image data.

At step S13, the profile data calculating portion 41a of the image processing apparatus 30 performs the profile extraction processing on the image-data which is outputted from the image reading apparatus to obtain pieces of profile data. At step S14, the binarizing processing portion 41b performs the binarizing processing on the profile data. Owing to this, profile points of a part, which has a difference in brightness more than a predetermined value, are selected.

At step S15, the convex closure processing portion 41c performs the convex closure processing on the pieces of profile data, which has been subjected to the binarizing processing, to extract the outermost profile points from the profile points selected by the binarizing processing. At step S16, the blackening processing portion 41d performs the blackening processing with respect to the area outside the irradiation field 4, the blank area 5 and the scattering area 6 as shown in FIG. 3, on the basis of the received image data and the profile data which has been subjected to the convex closure processing.

At step S17, the image processing portion 41e performs various image processing such as the normalizing processing and the gradation processing with respect to the image data which has been subjected to the blackening processing. At step S18, the image data, which has been subjected to the image processing, is recorded on the hard disk 43. Further, at step S19, the image is displayed on the display unit 32 or printed out by the printer 33 on the basis of the image data which has been subjected to the image processing.

As described above, according to the present invention, the outermost profile is extracted by carrying out the convex closure processing after the profile data obtained by profile extraction is binarized. Accordingly, even on the mammograph, it is possible to automatically carry out the blackening processing of the blank area and/or the scattering area by detecting the outermost profile of the mamma area.

The invention claimed is:

1. An image processing apparatus, comprising:
profile data calculating means for receiving image data obtained by imaging an object to calculate pieces of profile data corresponding to change of brightness among a plurality of pixels;
binarizing means for binarizing each of the pieces of profile data obtained by said profile data calculating means;

convex closure processing means for performing convex closure processing on the pieces of profile data binarized by said binarizing means to extract an outermost profile; and blackening processing means for performing blackening processing on the received image data to reduce brightness of pixels in an area out of the outermost profile extracted by said convex closure processing means.

2. An image processing apparatus according to claim 1, wherein said profile data calculating means calculates the pieces of profile data by using one of a Sobel filter and a Prewitt filter.

3. An image processing apparatus according to claim 1, wherein said convex closure processing means obtains a straight line which connects positions of two pixels included in the profile data binarized by said binarizing means to extract the outermost profile.

4. An image processing apparatus according to claim 1, wherein said convex closure processing means obtains a curved line which connects positions of at least three pixels included in the profile data binarized by said binarizing means to extract the outermost profile.

5. An image processing apparatus according to claim 1, wherein said convex closure processing means obtains a straight line which goes through among positions of at least three pixels included in the profile data binarized by said binarizing means to extract the outermost profile.

6. An image processing method, comprising the steps of:

(a) receiving image data obtained by imaging an object to calculate pieces of profile data corresponding to change of brightness among a plurality of pixels;

(b) binarizing each of the pieces of profile data obtained at step (a);

(c) performing convex closure processing on the pieces of profile data binarized at step (b) to extract an outermost profile; and (d) performing blackening processing on the received image data to reduce brightness of pixels in an area out of the outermost profile extracted at step (c).

* * * * *